(12) United States Patent
Donaldson (10) Patent No.: US 6,878,129 B2
(45) Date of Patent: Apr. 12, 2005

(54) ATRAUMATIC TEMPORARY ARTERIAL BRANCH PERFUSION DEVICE

(75) Inventor: Magruder C. Donaldson, Boston, MA (US)

(73) Assignee: Brigham and Women's Hospital, Boston, MA (US)

( * ) Notice: Subject to any disclaimer, the term of this patent is extended or adjusted under 35 U.S.C. 154(b) by 367 days.

(21) Appl. No.: 10/034,733

(22) Filed: Dec. 21, 2001

(65) Prior Publication Data

US 2003/0120205 A1 Jun. 26, 2003

(51) Int. Cl.[7] ............................................. A61M 31/00
(52) U.S. Cl. ................................... 604/93.01; 604/264
(58) Field of Search ........................... 604/93.01, 96.01, 604/103.01–103.04, 264, 523, 524, 532; 606/192–194

(56) References Cited

U.S. PATENT DOCUMENTS

| 3,802,432 A | * | 4/1974 | Djerassi ..................... 604/6.03 |
| 5,456,714 A | | 10/1995 | Owen |
| 5,769,870 A | | 6/1998 | Salahieh et al. |
| 5,925,054 A | | 7/1999 | Taylor et al. |
| 6,024,755 A | | 2/2000 | Addis |
| 6,048,333 A | * | 4/2000 | Lennox et al. ............... 604/113 |
| 6,152,948 A | | 11/2000 | Addis |
| 6,206,913 B1 | | 3/2001 | Yencho et al. |
| 6,210,365 B1 | | 4/2001 | Afzal |
| 6,214,022 B1 | | 4/2001 | Taylor et al. |
| 6,669,680 B1 | * | 12/2003 | Macoviak et al. .......... 604/509 |

* cited by examiner

*Primary Examiner*—Manuel Mendez
(74) *Attorney, Agent, or Firm*—William C. Geary, III; Nutter, McClennen & Fish

(57) ABSTRACT

A perfusion catheter system that allows selective temporary perfusion of small vascular or other anatomic structures arising from a host structure atraumatically. The perfusion device has an elongate body having an afferent end portion for receiving perfusion fluid, an efferent end portion for delivering the perfusion fluid to the branch vessel, and a lumen extending between the afferent and efferent end portions for the passage of fluid. The perfusion fluid is delivered through a hub assembly which provides a secure temporary water-tight seal between the perfusion catheter and the host structure without damage to the tissue, thereby enabling a safe and effective interface with small branch vessels during host artery clamping.

18 Claims, 5 Drawing Sheets

FIG. 8B

ATRAUMATIC TEMPORARY ARTERIAL BRANCH PERFUSION DEVICE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to perfusion catheters for use during cardiac and vascular surgeries. More specifically, the present invention relates to a perfusion catheter having a tissue-contacting interface that enables atraumatic sealing with a vessel wall for delivering perfusion fluid to peripheral blood vessels during surgery.

BACKGROUND OF THE INVENTION

One of the leading complications of cardiovascular disease is a condition known as atherosclerosis in which the arteries harden from fibrosis or calcification and/or narrow due to plaque formation within the arterial lumen. Patients who suffer from atherosclerosis are susceptible to developing aneurysms in certain regions of the body. These aneurysms, which are enlargements of the blood vessel caused by a weakening of the vessel wall, can often occur in areas such as the ascending aorta, aortic arch, thoracic aorta, or abdominal aorta. If left untreated, the aneurysm can grow and potentially rupture, causing massive hemorrhaging resulting in death.

Current modes for aneurysm repair require surgical intervention and frequently involve bypass grafting procedures. In a traditional aortic aneurysm repair, direct surgical access to the aneurysm is gained, after which the diseased portion of the vessel is excised and replaced with a prosthetic graft that is anastomosed, or reattached, to the healthy remainder of the aorta. Gaining in popularity is a minimally invasive technique whereby a sutureless vascular graft placed within the abdominal aorta spans the length of the aneurysm and provides a new pathway for blood flow through the diseased region of the vessel. In patients who are candidates for this minimally invasive procedure, a guidewire is introduced into the femoral artery after surgical exposure of the artery. Using fluoroscopic guidance, a catheter delivery system can be inserted over the guidewire and positioned across the aneurysm. Once the catheter is in place, a vascular prosthesis such as a compressed graft with self-expanding barbs at each end can be released at the diseased region. The barbs anchor the graft to the walls of the vessel, creating a circumferential seal at locations above and below the aneurysm to isolate the aneurysmal wall from intraluminal blood flow and pressure, thereby preventing further expansion of the aneurysm and decreasing the risk of rupture. Finally, the delivery catheter is removed, leaving the deployed prosthesis.

In both surgical procedures described above, branches which arise from the aneurysmal section of the involved artery are routinely excluded from the patient's circulation in order to adequately replace the weakened artery. When such branches are small or provide flow to tissues which have alternative blood supply from an artery arising from a region remote to the aneurysm, they can be sacrificed without complication. On the other hand, if the branches which arise from the aneurysm are critical to the normal function of vital organs, they must be protected during exclusion of the aneurysm and then restored to circulation by surgical reimplantation into the prosthetic graft. In the minimally invasive surgical method, there is at present no technique for protection and restoration of important branches which arise directly from the aneurysmal region of the aorta. Consequently, the presence of an important branch within the aneurysm is one of the criteria which can disqualify a patient from being a candidate for this minimally invasive surgery.

In the traditional surgical method, the aneurysmal section of the artery is temporarily clamped to stop flow in order to provide a blood-free field for the surgeon to operate. This clamping necessarily cuts off blood flow to vessels that branch from the clamped artery. When flow to the branch vessels cannot be preserved during clamping or restored promptly, damage to the tissue that rely on these branched vessels is likely. For example, one of the most devastating complications affecting about 10–15 percent of patients undergoing surgery to repair extensive aneurysms involving the thoracic and abdominal aorta together is paraparesis or paraplegia, a weakening or paralysis of the lower extremities caused by the temporary or permanent interruption of blood flow through small branches supplying the spinal cord. In this situation, arterial clamping prevents the thoracic intercostal arteries from feeding blood to the anterior spinal artery and adequate spinal blood flow must be derived from collateral arteries arising from other sources. Measures to protect the spinal cord from injury during clamping and prior to surgical reimplantation into the prosthetic graft include anticoagulation, use of a temporary aortic bypass or shunt, and neural protection using pharmacological agents, topical or systemic cooling, and spinal fluid drainage. All of these measures have proven helpful, but the risk of spinal cord injury has yet to be completely eliminated.

Moreover, there is an irreducible minority of patients who appear to be absolutely dependent on continuous blood flow to the spinal cord by way of the intercostal arteries. These individuals appear to require near-continuous temporary perfusion of the intercostal arteries during aortic clamping, followed by subsequent reimplantation of the intercostal arteries into the prosthetic graft, to avoid spinal ischemia. The chief impediment to this strategy has thus far been the lack of a reliable and satisfactory technique for the temporary perfusion of the intercostal arteries.

Currently available devices for temporary perfusion of the intercostal arteries require direct cannulation of these small vessels, which are typically 1–2 mm in diameter. Direct cannulation can be unwieldy and cumbersome, often producing inadequate sealing between the cannula and the vessel which results in poor flow into the vessel and a high likelihood of permanent vessel damage. There is thus a need for a new perfusion device that is designed to solve the problem of safely and effectively interfacing with small branch vessels such as the intercostal arteries. Specifically, there is a need for a perfusion catheter that allows adequate continuous selective temporary blood flow to small vascular branches during aortic clamping without causing injury to the vessels themselves.

SUMMARY OF THE INVENTION

The present invention overcomes the drawbacks inherent in prior surgical methods and devices by providing a perfusion catheter system that allows selective temporary atraumatic perfusion of small vascular or other anatomic structures such as intercostal arteries. The perfusion catheter of the present invention has an elongate body having an efferent end portion, an afferent end portion, and a lumen within the elongate body that extends between the efferent and afferent end portions for the passage of fluid. At the afferent end portion is an inflow port in communication with the lumen. The inflow port receives perfusion fluid and can be configured to be coupled to a perfusion source. The perfusion fluid is delivered through a hub assembly located at the efferent end portion of the elongate body and which is in communication with the lumen. The hub assembly provides a secure temporary water-tight seal between the perfusion catheter and an anatomic surface without damage to the tissue, thereby enabling a safe and effective interface for perfusion of small branch vessels arising from that surface.

The hub assembly can comprise a flexible chamber that extends from the efferent end portion of the elongate body. Surrounding the flexible chamber is a conformable contact ring that is adapted for placement over the origin of a branch vessel, i.e., where the small branch vessel intersects the larger host artery. In one embodiment of the present invention, the hub assembly is held on the inner surface of the host artery adjacent to the opening, or origin, of the branch vessel, using a closure device. The closure device can include a spring clamp that applies mechanical pressure on the conformable contact ring over the opening of the branch vessel. The spring clamp can comprise a base configured to seat behind the host artery around the portion of the branch vessel outside the host artery. Extending from the base is an elevated arm configured to surround and exert closure pressure on the conformable contact ring against the inner surface of the host artery. Both the base and the contact ring can be shaped like C-rings.

In another embodiment of the present invention, the conformable contact ring includes a magnetic insert and the closure device is a magnetic ring that can be placed on an outer surface of the host artery, around the portion of the branch vessel outside the host artery. The magnetic ring is of sufficient strength to effect magnetic attraction of the contact ring against the inner surface of the host artery to create a seal around the origin of the branch vessel.

In yet another embodiment of the present invention, the perfusion catheter includes a suction channel that extends through the afferent catheter apparatus and into a concave contact ring. A connector port on the catheter that is attached to the suction channel is configured for coupling with a vacuum source. The suction channel is in communication with the conformable concave contact ring so that a vacuum pressure can be applied to the ring. This suction enables the conformable concave contact ring to form a water-tight, atraumatic seal between the hub and the inner surface of the host artery adjacent to the origin of the branch vessel.

Further features of the invention, its nature and various advantages will be more apparent from the accompanying drawings and the following detailed description of the drawings and the preferred embodiments.

DETAILED DESCRIPTION OF THE INVENTION

Figure 1:
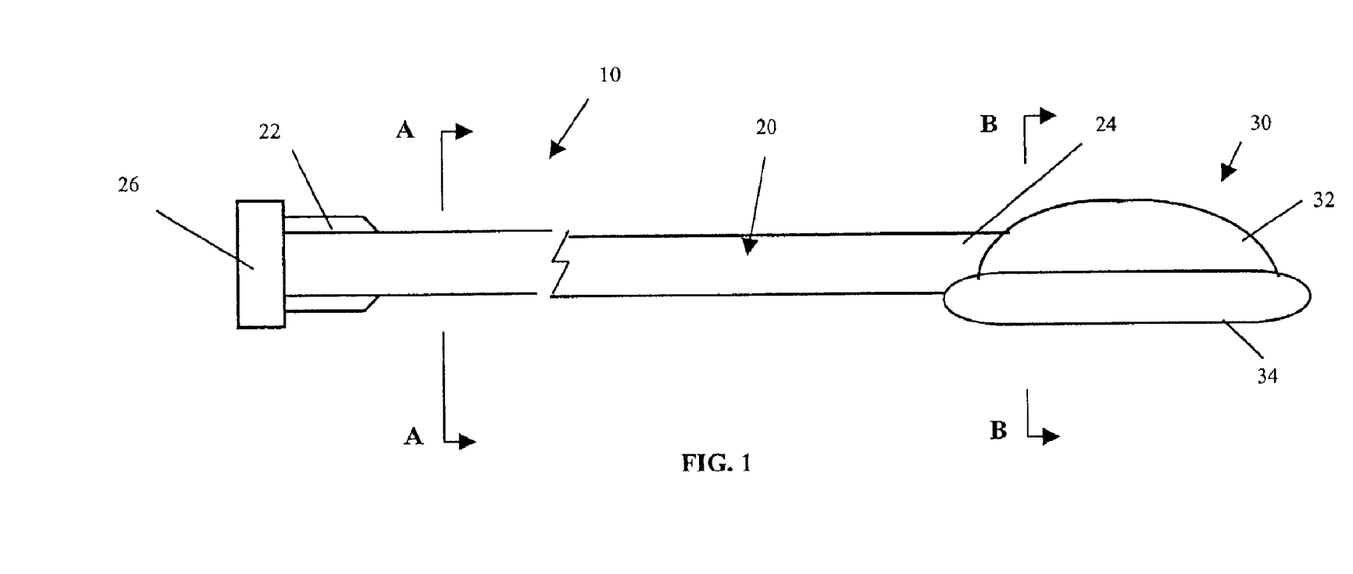
FIG. 1 is a side view of an embodiment of the perfusion device of the present invention.
Figure 2A:
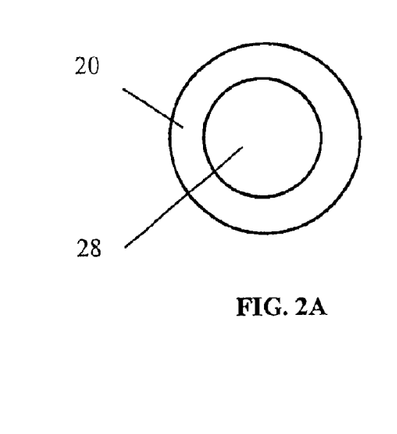
FIG. 2A is a cross-sectional view of the device of FIG. 1 along lines A—A.

Referring now to the drawings and particularly to FIG. 1, an exemplary perfusion device 10 of the present invention is shown. The perfusion device 10 allows selective temporary perfusion of small vascular or other anatomic structures such as intercostal arteries atraumatically during surgeries where the main artery is clamped and blood flow to these branch vessels is interrupted. The device 10 includes a catheter defined by an elongate body 20 extending between an afferent end portion 22 and an efferent end portion 24. The elongate body is preferably formed from a flexible biocompatible material to allow ease of surgical manipulation. The afferent end portion 22 is configured to attach to a suitable source of perfusion fluid. For instance, the afferent end portion 22 can include an inflow port 26 having a Luer lock connector (not shown) for attaching to the base ring of a conformable perfusion chamber containing perfusion fluid, which would also be attached by intravenous or perfusion tubing to a standard type pressure pump. The inflow port 26 is also in fluid communication with a lumen 28 extending between the afferent end portion 22 and efferent end portion 24 for passage of the perfusion fluid through the elongate body 20, as shown in FIG. 2A.

Figure 2B:
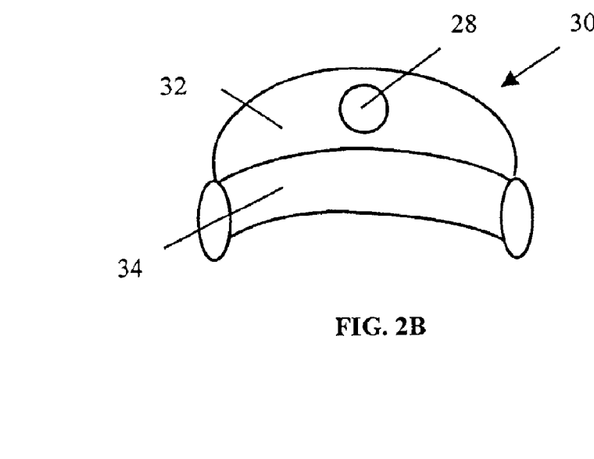
FIG. 2B is a cross-sectional view of the device of FIG. 1 along lines B—B.
Figure 3:
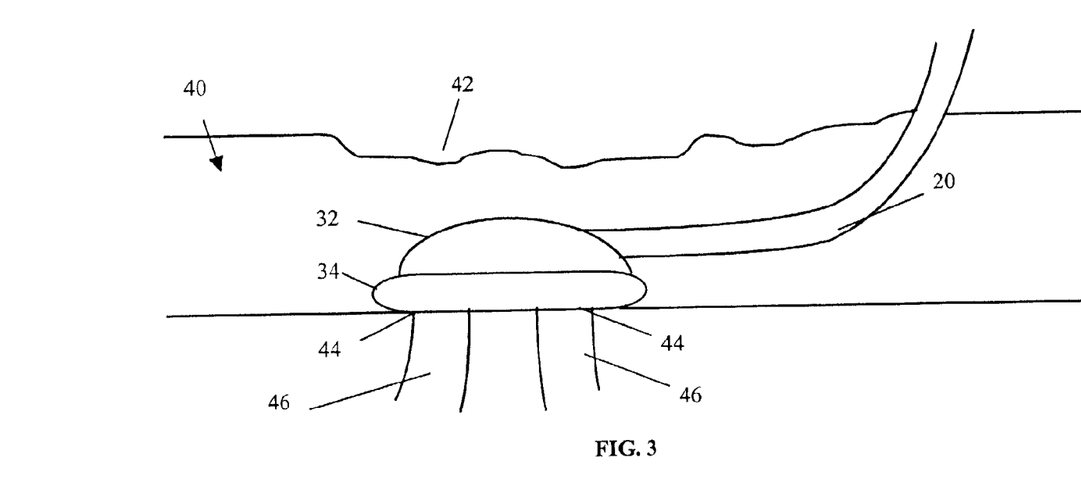
FIG. 3 is a perspective view of the device of FIG. 1 deployed in an artery.
Figure 4:
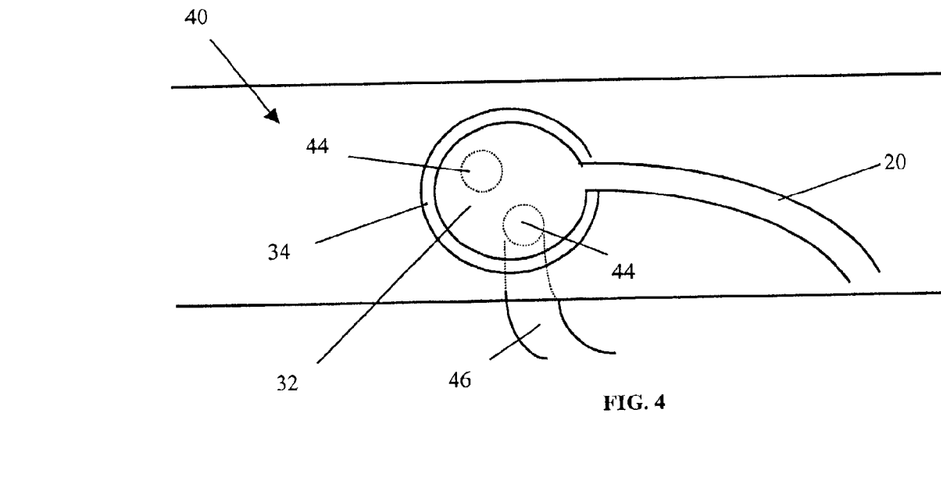
FIG. 4 is a top-down view of the device of FIG. 3.

At the efferent end portion 24 is a hub assembly 30 defining an outflow port and being in communication with the lumen 28, as illustrated in FIG. 2B. Hub assembly 30 includes a flexible chamber 32 extending from the efferent end portion 24 and includes the opening to lumen 28 for delivering perfusion fluid. Surrounding the flexible chamber 32 is a conformable contact ring 34 adapted for placement over the origin 44 of a branch vessel 46. Conformable contact ring 34 is formed of a soft biocompatible material and can have a circular or oval shape to provide atraumatic contact with the inside of the host artery 40 from which branch vessels 46 originate. As shown in FIG. 3, the hub assembly 30 can be placed within an opening 42 created by a surgical arterotomy of the host artery 40 that has been clamped. The conformable contact ring 34 can be applied to the inner surface of the host structure, or artery 40 and placed over the origins 44 of the branch arteries 46 that stem from the host artery 40. Conformable contact ring 34 is sized and configured to cover and seal off at least one origin 44, but can also be sized and configured to cover more than one origin 44, as illustrated in FIG. 4.

Figure 5A:
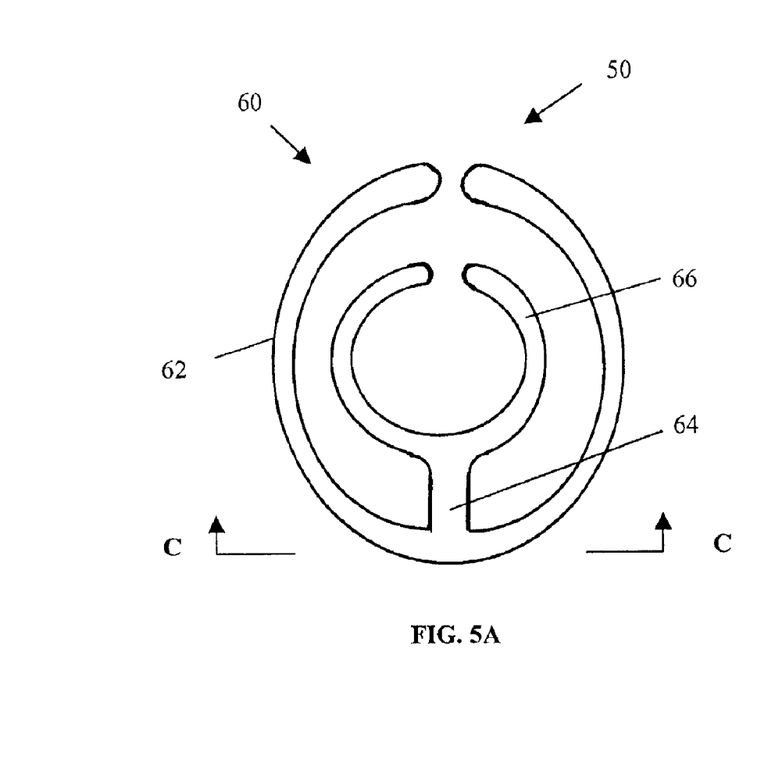
FIG. 5A is a top-down view of an embodiment of a coupling device of the present invention.
Figure 5B:
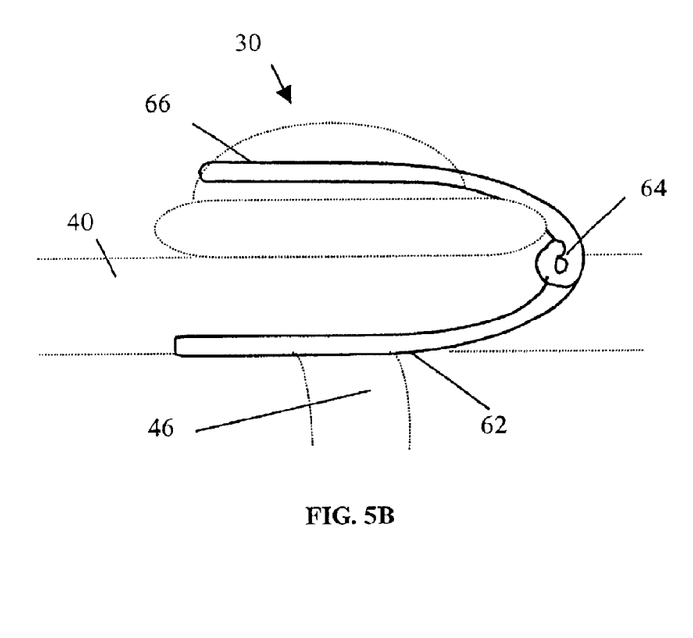
FIG. 5B is a side view of the coupling device of FIG. 5A along lines C—C in a deployed state.

To ensure that the hub assembly 30 provides a water-tight seal with the inner surface of the host artery 40 as perfusion fluid is delivered to the origins 44 of the branch vessels 46, a low-profile coupling device 50 can be used with the hub assembly 30. In one embodiment, the coupling device 50 can comprise a spring clamp 60 for applying mechanical pressure on the conformable contact ring 34. Spring clamp 60 can comprise a base 62 configured to seat behind the host artery 40 around the portion of the branch vessel 46 outside the host artery 40, and an elevated arm 66 extending from the base 62. Elevated arm 66 is configured to surround and exert closure pressure on the conformable contact ring 34 against the inner surface of the host artery 40. Spring clamp 60 can also include a coiled portion 64 between the base 62 and elevated arm 66 to import flexibility to the clamp 60. It is contemplated that both base 62 and elevated arm 66 can be shaped like C-rings. However, both the base 62 and elevated arm 66 can be differently shaped. For instance, a V-shape or U-shape would also work as well for the base 62 and elevated arm 66. As shown in FIG. 5B, the base 62 can be slid under the host artery 40 such that the base 62 partially encircles or surrounds the target branch vessel 46. The elevated arm 66 will then be positioned over the hub assembly 30, pressing down against the conformable contact ring 34 such that an atraumatic, water-tight seal is formed with the inner surface of the host structure 40.

Figure 6A:
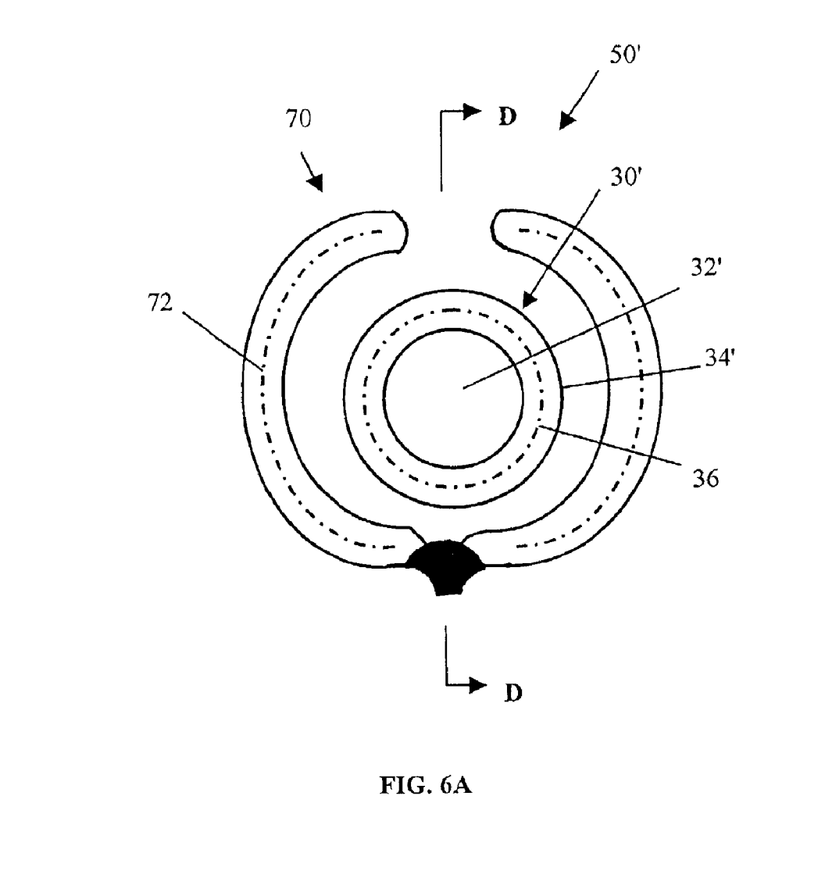
FIG. 6A is a top-down view of another embodiment of a coupling device of the present invention.
Figure 6B:
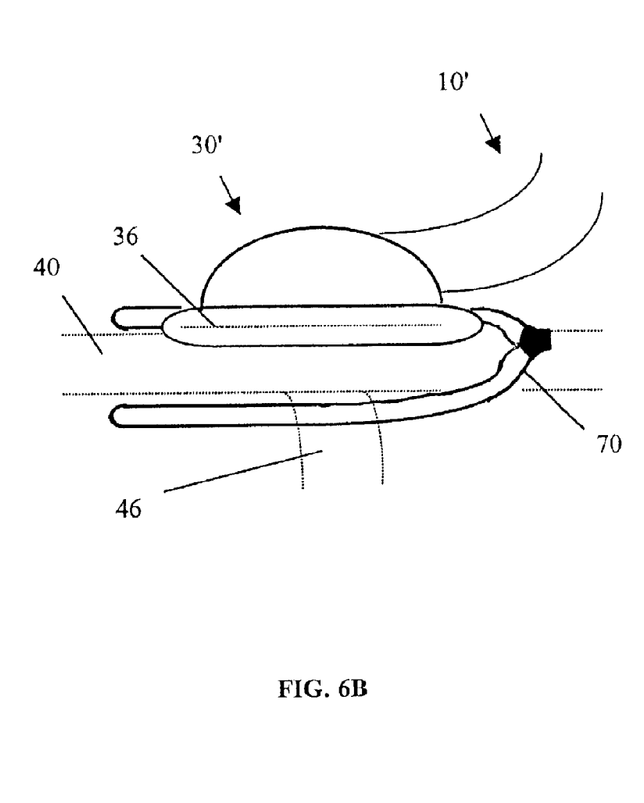
FIG. 6B is a side view of the closure device of FIG. 6A along lines D—D in a deployed state.

In another embodiment of the present invention, perfusion device 10' includes a hub assembly 30' that uses a magnetic mechanism for creating the seal with the inner surface of the host artery 40. In all other respects, perfusion device 10' has the same elements as perfusion device 10, with similar elements having the same numerical designation followed by the prime symbol. Hub assembly 30' has a conformable contact ring 34' that includes a magnetic insert 36, as illustrated in FIG. 6A. This magnetic insert 36 works in conjunction with a coupling device 50' comprising a magnetic ring 70. The magnetic ring 70 can comprise magnetic material 72 formed into a C-ring. However, the magnetic ring 70 can also have a U-shape or V-shape. Magnetic ring 70 can also be partially circular. To create the seal between the hub assembly 30' and the inner surface of the host artery 40, conformable contact ring 34' is placed against the inner surface of the host artery adjacent to the origin of the branch vessel 46. Then, magnetic ring 70 is placed behind the host artery 40 and around the branch vessel 46, as illustrated in FIG. 6B. The magnets 36, 72 are of sufficient strength to ensure an atraumatic, water-tight seal with the host artery wall.

Figure 7:
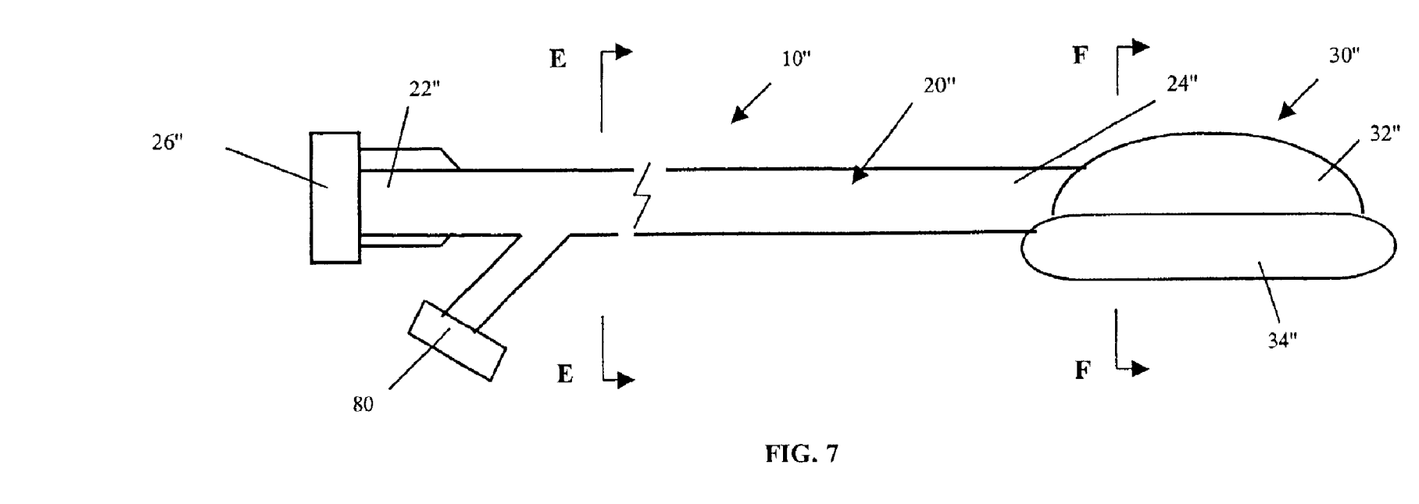
FIG. 7 is a side view of another embodiment of the perfusion device of the present invention.
Figure 8A:
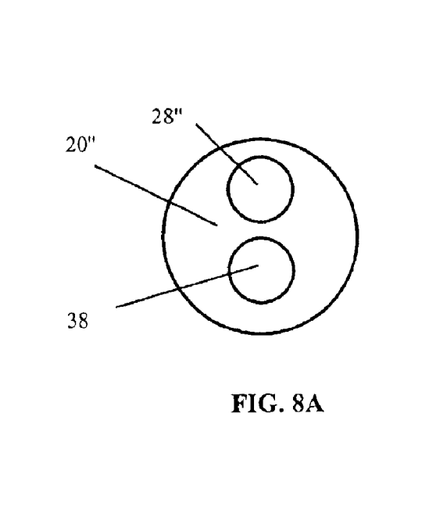
FIG. 8A is a cross-sectional view of the device along lines E—E.
Figure 8B:
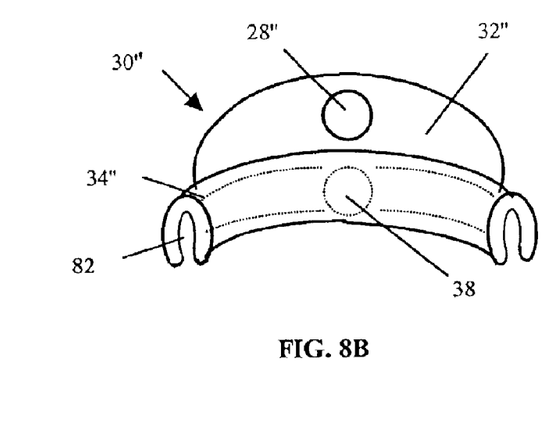
FIG. 8B is a cross-sectional view of the device along lines F—F.

In yet another embodiment of the present invention, perfusion device 10" utilizes still another mechanism for creating the seal with the inner surface of the host artery 40. FIG. 7 shows a perfusion device 10" having an additional suction port 80 configured for attaching to a low vacuum source. In all other respects, perfusion device 10" has the same elements as perfusion device 10, with similar elements having the same numerical designation followed by the double prime symbol. The suction port 80 is in communication with a suction channel 38 extending from the port 80 through the elongate body 20" to a conformable concave contact ring 34". As shown in FIG. 8A, the elongate body 20" can be coaxial and contain both the lumen 20" and suction channel 38. In this particular embodiment, conformable contact ring 34" is not a closed loop but rather forms a concavely-shaped ring 82, as illustrated in FIG. 8B. Continuous aspiration through the suction channel 38 enables the conformable concave contact ring 34" to form an atraumatic, water-tight seal with the inner surface of the host artery 40 without the necessity of a coupling device 50. Nevertheless, it is contemplated that a coupling device 50 can still be used to enhance the external pressure against the conformable concave contact ring 34" against the wall of the host structure 40.

The perfusion devices 10, 10', 10" of the present invention thus provide means for safe and effective perfusion of small branch vessels such as the intercostal arteries during surgeries where flow is necessary through these small branches. By enabling continuous, selective and temporary blood flow through the branch vessels during aortic clamping, the perfusion devices of the present invention prevent damage to the tissues being fed by these branch vessels and which require uninterrupted flow, without causing injury to the branch vessels themselves. And, because the perfusion devices of the present invention are sufficiently low-profile and soft, the devices are easy to surgical manipulation during perfusion. The flexibility of the device 10 enables rapid cessation of perfusion, detachment and removal of the hub assembly 30, 30', and 30" and coupling device 50, 50' near the conclusion of the portion of the surgical procedure designed to reimplant the branch vessel origins. Fluid flow can thus be reestablished by reimplantation of the branch vessels with minimal interruption of continuous flow to the branch vessels.

It is understood that, in most cases, the perfusion fluid would be heparinized blood. However, other fluids such as electrolyte solution, culture medium, or pharmacological preparations can also be applied using the perfusion devices of the present invention. In addition, the perfusion could be driven by gravity, an infusion pump or cardiac action. For example, a prosthetic graft, a regional artery or a pump oxygenator could serve as a convenient and suitable source of blood in some situations.

It is also understood that the proposed perfusion device 10 of the present invention can be constructed in various calibers, sizes, shapes, and profiles. Further, the same perfusion techniques described above may be used in aortic branches such as the mesenteric, renal or internal iliac arteries. The perfusion device 10 of the present invention may be applied to the origins of the innominate, left carotid and subclavian vessels using a correspondingly larger hub and catheter caliber suitable for higher flows during aortic arch repairs. Finally, the perfusion device 10 of the present invention may also be used in vascular, hepatobiliary, or urological surgeries where secure atraumatic temporary perfusion of an important anatomic structure is desirable.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A perfusion catheter system for selectively and temporarily delivering perfusion fluid to a branch vessel originating from a host structure, comprising:

an elongate body having an efferent end portion, an afferent end portion, a lumen extending therebetween for passage of fluid therethrough;

an inflow port at the afferent end portion in communication with the lumen and being configured to be coupled to a perfusion source to receive perfusion fluid; and a hub assembly defining an outflow port at the efferent end portion in communication with the lumen to deliver the perfusion fluid to the branch vessel, the hub assembly being configured for placement over the origin of the branch vessel;

wherein the hub assembly provides a water-tight, atraumatic seal with an inner surface of the host structure adjacent the origin of the branch vessel.

2. The system of claim 1, wherein the hub assembly comprises a flexible chamber extending from the efferent end portion of the elongate body, the flexible chamber being surrounded by a conformable contact ring adapted for placement over the origin of the branch vessel.

3. The system of claim 2, further including a spring clamp for applying mechanical pressure on the conformable ring over the origin of the branch vessel.

4. The system of claim 3, wherein the spring clamp comprises a base and an elevated arm extending from the base, the base being configured to seat behind the host structure and around the branch vessel, and the elevated arm being configured to surround and bear down on the contact ring against the inner surface of the host structure.

5. The system of claim 4, wherein the base and the elevated arm are shaped like C-rings.

6. The system of claim 2, wherein the contact ring includes a magnetic insert.

7. The system of claim 6, further including a magnetic ring for placement on an opposite surface of the host structure behind the contact ring, the magnetic ring being of sufficient strength to effect magnetic attraction of the contact ring against the surface of the host structure for the origin of the branch vessel.

8. The system of claim 2, wherein the contact ring is concave and has a suction channel extending therefrom, the suction channel being attached to a vacuum for applying a vacuum pressure to the contact ring.

9. The system of claim 1, wherein the perfusion source is heparinized blood.

10. A perfusion catheter system for selectively and temporarily delivering perfusion fluid to a branch vessel originating from a host structure, comprising:
   an elongate body having an efferent end portion, an afferent end portion, and a lumen extending therebetween for passage of fluid therethrough, the afferent end portion being configured to be coupled to a perfusion source to receive perfusion fluid;
   a hub extending from the efferent end portion and being in communication with the lumen to deliver the perfusion fluid to the branch vessel, the hub being surrounded by a conformable contact ring adapted for placement over the opening of the vessel; and
   a coupling device for maintaining the conformable contact ring in position;
   wherein the conformable contact ring and coupling device form a water-tight, atraumatic seal between the hub and an inner surface of the host structure of the branch vessel.

11. The system of claim 10, wherein the hub includes a flexible chamber.

12. The system of claim 10, wherein the coupling device includes a spring clamp for applying mechanical pressure on the conformable contact ring over the opening of the branch vessel.

13. The system of claim 12, wherein the spring clamp comprises abase and an elevated arm extending from the base, the base being configured to seat behind the host structure around the branch vessel, and the elevated arm being configured to surround and bear down on the conformable contact ring.

14. The system of claim 13, wherein the base and the elevated arm are shaped like C-rings.

15. The system of claim 10, wherein the conformable contact ring includes a magnetic insert.

16. The system of claim 15, wherein the coupling device includes a magnetic ring for placement on an opposite surface of the host structure behind the conformable contact ring, the magnetic ring being of sufficient strength to effect magnetic attraction of the conformable contact ring over the opening of the branch vessel.

17. A perfusion device for selectively and temporarily delivering perfusion fluid to a branch vessel originating from a host structure, comprising:
   an elongate body having an efferent end portion, an afferent end portion, and a lumen extending therebetween for passage of fluid therethrough, the afferent end portion being configured to be coupled to a perfusion source to receive perfusion fluid;
   a hub extending from the efferent end portion and being in communication with the lumen to deliver the perfusion fluid to the branch vessel, the hub being surrounded by a conformable concave contact ring adapted for placement over the origin of the branch vessel; and
   a suction channel extending through the elongate body and having a connector port for coupling with a vacuum source, the suction channel being in communication with the conformable concave contact ring for applying a vacuum pressure such that the conformable concave contact ring forms a water tight, atraumatic seal between the hub and the host structure of the branch vessel.

18. The device of claim 17, wherein the hub includes a flexible chamber.

* * * * *

UNITED STATES PATENT AND TRADEMARK OFFICE
CERTIFICATE OF CORRECTION

PATENT NO. : 6,878,129 B2  
APPLICATION NO. : 10/034733  
DATED : April 12, 2005  
INVENTOR(S) : Magruder C. Donaldson Page 1 of 1

It is certified that error appears in the above-identified patent and that said Letters Patent is hereby corrected as shown below:

In the Specification at column 1, line 12 delete "Not Applicable." and insert the following:

This invention was made with Government support under Grant No. DAMD17-02-2-0006 awarded by the U.S. Department of the Army. The U.S. Government has certain rights in this invention.

Signed and Sealed this

Eighteenth Day of March, 2008

JON W. DUDAS  
*Director of the United States Patent and Trademark Office*